United States Patent
Muchnik

(10) Patent No.: US 7,511,832 B2
(45) Date of Patent: *Mar. 31, 2009

(54) SPECIFIC DENSITY DETECTOR AND OPTICAL MULTIPLEXER IMPROVEMENT

(75) Inventor: Boris J. Muchnik, Denver, CO (US)

(73) Assignee: Nuclear Solutions, Inc., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/048,042

(22) Filed: Jan. 31, 2005

(65) Prior Publication Data

US 2006/0082788 A1 Apr. 20, 2006

Related U.S. Application Data

(63) Continuation-in-part of application No. 10/965,164, filed on Oct. 14, 2004.

(51) Int. Cl.
*G01J 1/00* (2006.01)
*G01J 1/42* (2006.01)
(52) U.S. Cl. ............... 356/614; 356/152.3; 356/213
(58) Field of Classification Search .......... 356/614, 356/152, 345, 358, 4.01, 5.01, 152.3, 213; 372/19, 33; 359/223, 198, 850, 212; 250/216, 250/234
See application file for complete search history.

(56) References Cited

U.S. PATENT DOCUMENTS

| | | | | |
|---|---|---|---|---|
| 4,641,950 | A * | 2/1987 | Rongen et al. | 347/243 |
| 4,732,472 | A * | 3/1988 | Konig et al. | 356/152.3 |
| 4,839,525 | A * | 6/1989 | Kano et al. | 250/559.21 |
| 5,258,821 | A * | 11/1993 | Doggett et al. | 356/496 |
| 5,331,649 | A * | 7/1994 | Dacquay et al. | 372/23 |
| 5,638,189 | A * | 6/1997 | Yanagisawa | 358/481 |
| 5,877,884 | A * | 3/1999 | Yanagisawa | 359/198 |
| 6,229,639 | B1 * | 5/2001 | Ozarski et al. | 359/223 |
| 6,233,045 | B1 * | 5/2001 | Suni et al. | 356/28.5 |

* cited by examiner

*Primary Examiner*—Sang Nguyen
(74) *Attorney, Agent, or Firm*—Michael L. Greenberg, Esq.; Greenberg & Lieberman, LLC

(57) ABSTRACT

An object is placed at a particular distance away from the nonreflecting side of a mirror, such that the gravitational force of the object affects the mirror. A laser is then pointed at the opposite, reflecting side of the mirror, thereby itself reflecting off the mirror and going back in to the cavity of the laser, creating a mode-hopping effect. The mirror will be affected by three forces, the force of a spring ($F_S$), the force of a modulating signal ($F_{MS}$), created by an electro mechanical device attached to the mirror, and the gravitational force of objects as they approach and recede away from the mirror.

3 Claims, 1 Drawing Sheet

SPECIFIC DENSITY DETECTOR AND OPTICAL MULTIPLEXER IMPROVEMENT

Priority is hereby claimed to U.S. patent application Ser. No. 10/965,164 filed on Oct. 14, 2004.

FIELD OF THE INVENTION

The present invention is a system for detecting the specific density of objects, and more particularly, identifying objects according to their specific density.

BACKGROUND OF THE INVENTION

Detection of objects is important in many applications. For example, for security reasons, detection of objects is important to avoid allowing banned objects from entering and/or exiting a building, plane, or other location. Detection of objects can be difficult, however, if the detection is merely visual, as objects can easily be concealed from view. Thus, entrances to courthouses employ metal detectors to detect any sort of gun, knife of other typically metallic dangerous weapon.

Detection of metallic objects is not adequate for many security applications, as there are many objects that are undesirable that are not metallic whatsoever. And if visual inspection is not adequate to properly detect undesirable objects, then there is a need for a system that can accurately detect objects or else undesirable objects will remain undetected.

Detection of objects is also important for tracking or identification purposes wholly separate from security. It is desirable to correctly identify an object so that its movement can be accurately tracked, even when there is no viable means of placing a tracer, beacon, or other identification marking or code on the object. Thus, there is a need for a system that can detect an object so that the object's movement can be tracked without placing tracking means on the object.

Any object detection system relies on a property or characteristic of an object. For example, if the detection system is visual, the contour or the color of an object might be relied upon to detect certain objects. The specific density is one of many properties of an object, and remains static. Once an object's specific density is known, that object can be detected. However, the problem remains how to detect the specific density of an object if that object is not to be disturbed. Thus, there is a need for system for detecting the specific density of an object so that the object can be identified, wherein the object remains undisturbed.

The present invention deals with two high level concepts that are common in the art. The first concept is mode-hopping. Mode-hopping is an energy transfer from one transverse electronic mode (TEM) to another. For example, the most common mode hopping occurs between the fundamental mode (TEM00) and the donut mode (TEM01). Mode-hopping has been observed in semiconductor lasers due to the laser light fed back in to the laser cavity as a result of reflections. The laser energy distribution in a beam will switch from one mode to another as a function of the laser light fed back in to the cavity.

Inventions that discuss the mode-hopping phenomenon usually discuss the negative aspects. Mode-hopping is seen as a drawback to most lasers, particularly as it deals with an increase in temperature. Mode-hopping creates a situation by which, for a given pumping current, the laser can hop to a completely different mode. This "instability" has been linked to the occurrence of unwanted intensity noise, a change in injection strength (detuning), a reduction in beam power, and overall distress to users of various mechanisms utilizing lasers (including semiconductor lasers in compact disc players and bar-code scanners).

Mode-hopping has also been connected to problems other than use of lasers. In telecommunications, the switching from one mode to another affects the maximum data transmission rate, because different wavelengths have different velocities in single-mode fibers with high dispersion.

The second concept common in the art is the gravity meter, also known as a gradiometer. The concept of gradiometers has been known for some considerable time. Gradiometers measure the differential curvature or ellipticity of gravity equipotential surfaces, the rate of change of the increase of gravity in the horizontal direction, and/or the rate of increase of gravity in the vertical direction. Their object is to measure small changes in the acceleration of a mass due to gravity, known as "g". Through discovery of "g", one can determine the mass, specific density, etc. of a given space.

While gradiometers provide a method by which to obtain data regarding spaces, particularly dealing with land surveillance, most gradiometers have been expensive to manufacture and are unsuitable for long-term installation in the field. Because of the expense, care and accuracy that need to be put into their use, gradiometers are not suitable for everyday use. Furthermore, the gravity gradient measurements are associated with significant noise patterns.

SUMMARY OF THE INVENTION

The present invention introduces mode-hopping as a method by which one can determine the specific density of an object at a distance. An object is placed at a particular distance away from the nonreflecting side of a mirror, such that the gravitational force of the object affects the mirror. A laser is then pointed at the opposite, reflecting side of the mirror, thereby itself reflecting off the mirror and going back in to the cavity of the laser, creating a mode-hopping effect. The mirror will be affected by three forces, the force of a spring ($F_S$), the force of a modulating signal ($F_{MS}$), created by an electro mechanical device attached to the mirror, and the gravitational force of objects as they approach and recede away from the mirror.

Attached to the laser will be a microprocessor that will record the occurring mode-hopping activity. Because the gravitational force imposed on the mirror will change due to the gravitational force of the moving object ($F_{MU}$) as a result of the distance changing between the mirror and the object, it is necessary for either the present invention or the object to move because it is the change in the distance that is being measured—and without the movement the present invention will not function. The present invention will take into consideration $F_S$, $F_{MS}$, $F_{MU}$ and the distance between the object and the mirror, the change in the gravitational force on the mirror is calculated and plotted on a graph. By taking the second derivative of that function, the rate of change of the gravitational force between the mirror and the object is deducted, which is proportional to the specific density of the object.

A use for the present invention, though clearly not limited to such use, is for detection of nuclear bombs and other heavy metal devices before or when they come in to the country.

DETAILED DESCRIPTION OF THE PREFERRED EMBODIMENTS

Figure 1:
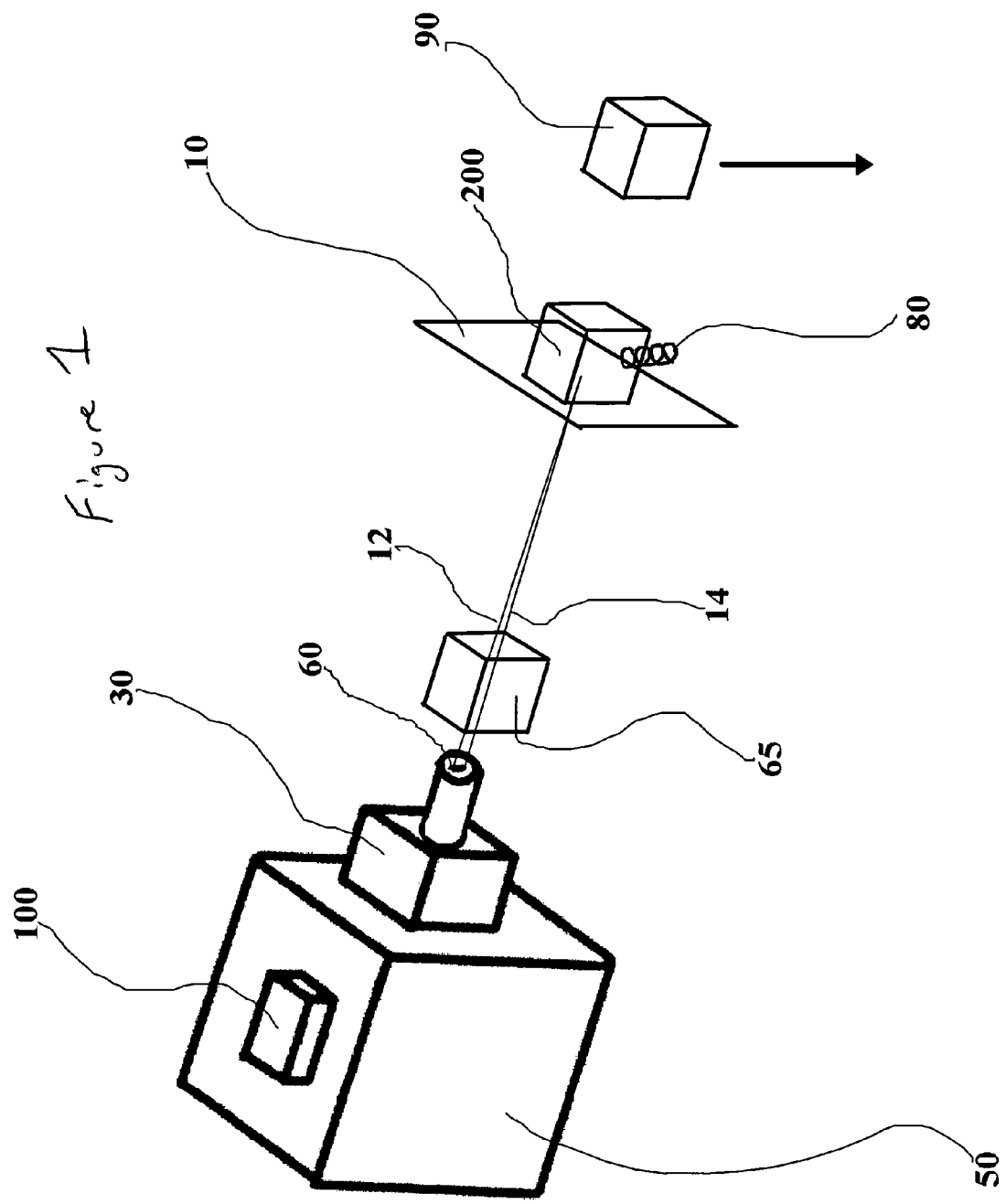
FIG. 1 shows an environmental perspective view of the present invention.

The present invention contains a (HSL) laser (50), which emits laser beams (12) towards an asymmetrically mounted mirror (amm) (10); the mirror (10) is positioned such that the reflecting side is facing towards the laser (50). The heterostructure laser (50) emits beams (12) that enter a collimating lens (30), which is normally part of the commercially available semiconductor lasers. The collimating lens (30) directs the beams (12) such that they are directed in a straight line towards the mirror (10). The emitted beams (12) then go through a narrow slit (60). The emitted beams (12) then reflect off the mirror (10), reflecting back to the laser (50), and the elements of the return beams (14) which go through the narrow slit (60) will go back in to the cavity of the laser (50), thereby creating a mode-hopping effect and depressing the single mode hopping mode. The system is optically aligned to maximize the effect of suppressing the single fundamental mode. This minimizes the emitted beams (12) of the laser (50). Any misalignment of the mirror (10) will cause the increase in the intensity of the output of the emitted beams (12).

The mirror (10) is mounted as part of the present invention, asymmetrically, via a spring (80) that allows the mirror (10) to move. The return beams (14) are reflected off the mirror (10) in different directions as a result of the movement of the mirror (10). While most of the return beams (14) do not get reflected back into the laser (50), the narrow slit (60) serves to ensure that when return beams (14) are in the correct position, as much light as possible is reflected back into the laser (50) in order to ensure the return beams (14) enter the laser cavity of the laser (50) and mode hopping is maximized.

On the opposite, nonreflecting side of the mirror (10) will be an object (90). The object (90) will have its own gravitational force ($F_{MU}$). The gravitational force will then be established between the mirror (10) and the object (90). This gravitational force will change as a result of moving the object (90) in the perpendicular direction to the axis of the mirror (10). Due to the change in the distance between the object (90) and the mirror (10), according to Newton's gravitational law the gravitational force is inversely proportional to the square of the distance. This changing force will produce a change in the orientation of the mirror (10), which will subsequently misalign the original optical setup described above. That angle of misalignment, which is proportional to the gravitational force will cause an increase in the return beams (14) and subsequently will become the measure of the gravitational force. The return beams (14) will be then detected and plotted as a function of the changing gravitational force. The second derivative of this plot will be proportional to the specific density of the object (90) and will be deducted electronically by the microprocessor (100) based on the above described measurements. The second derivative of different materials would be associated with specific densities, which will be then calibrated and stored in the microprocessor (100) for comparison to real time objects. Therefore, the microprocessor (100) will be able to distinguish between materials of interest, such as heavy metals or any other object or the lack thereof.

It should be understood that the change in the angle of the mirror and therefore the return beams (14) coming off the mirror (10) is extremely small due to the fact that the gravitational force between the object (90) and the mirror (10) is marginally measurable. Nevertheless, there are numerous methods for amplifying this effect that are commonly known. One of these techniques would be the use of an optical multiplexer (65) commonly used in the telecommunications industry. Optical multiplexers (65) are designed to amplify the input laser beam angle by virtue of multiple internal reflections. Any of the other commonly known methods for such amplification are included in this patent by reference, and are described in more detail below.

The mode-hopping is detected out of laser (50) is the same as that used in a standard cd player. Detection method is that as conventionally known.

The force of gravity is weakest of the fundamental forces, and therefore the "swing" of the laser (50), which is the difference between angle of the emitted beams (12) and the return beams (14), will necessarily quite small. Hence, a method to amplify the swing of the laser (50), beyond that which has already been described, is needed. Quite simply, amplification of the swing of laser (50) will ensure that the smallest of swings can be detected.

One method of amplification is to attach an optical multiplexer (65) to the present invention. The optical multiplexer (65) can be any conventional optical multiplexer, and its purpose is to multiply the angle Theta, of the swing of the laser (50), before return beams (14) return to the narrow slit (60). The emitted beams (12) have a Theta that will be equal to the Theta of the return beams (14) times two times the number of internal reflections in the optical multiplexer (65). This technique would increase the sensitivity of the detection scheme of the present invention.

The microprocessor (100) distinguishes between materials of interest, such as heavy metals or any other object or the lack thereof.

The present invention is not limited to the embodiments described above, but also has all embodiments within the scope of the following claims.

I claim:

1. A specific density detector, comprising:
   a laser, fired from a cavity;
   a mirror, positioned to reflected a laser beam produced by said laser back toward said laser, and into said cavity;
   a spring, in communication with said mirror;
   a collimating lens, in communication with said laser;
   a narrow slit disposed between said laser and mirror;
   a microprocessor, in communication with said laser, for said specific density of an object; and
   a multiplexer, positioned between said mirror and microprocessor.

2. A method for detecting specific density, comprising:
   firing a first laser beam at a front side of a mirror, said first laser beam fired from a cavity;
   passing an object past a backside of said mirror;
   measuring mode hopping in said cavity;
   plotting a second laser beam, said second laser beam being said first laser beam reflected from said mirror, as a function of the changing gravitational force of said object;
   determining a second derivative from plotting said laser beam as a function of the changing gravitational force of said object;
   determining a specific density of said object in proportion to said second derivative; and
   mounting a multiplexer in a manner so as to augment the swing of said first laser beam and said second laser beam.

3. The method of claim 2, further comprising mounting said mirror in a flexible fashion so that said mirror moves in response to passing the object past the backside of said mirror.

* * * * *